(12) United States Patent
Azpiroz et al.

(10) Patent No.: US 10,386,331 B2
(45) Date of Patent: Aug. 20, 2019

(54) PARTICLE MANIPULATION AND TRAPPING IN MICROFLUIDIC DEVICES USING TWO-DIMENSIONAL MATERIAL

(71) Applicant: International Business Machines Corporation, Armonk, NY (US)

(72) Inventors: Jaione Tirapu Azpiroz, Rio de Janeiro (BR); Michael Engel, Ossining, NY (US); Mathias B. Steiner, Rio de Janeiro (BR)

(73) Assignee: International Business Machines Corporation, Armonk, NY (US)

( * ) Notice: Subject to any disclaimer, the term of this patent is extended or adjusted under 35 U.S.C. 154(b) by 585 days.

(21) Appl. No.: 15/093,816

(22) Filed: Apr. 8, 2016

(65) Prior Publication Data
US 2017/0292934 A1 Oct. 12, 2017

(51) Int. Cl.
*G01N 27/447* (2006.01)
*B01L 3/00* (2006.01)
(Continued)

(52) U.S. Cl.
CPC .... *G01N 27/44773* (2013.01); *B01L 3/50273* (2013.01); *B01L 3/502715* (2013.01); *B01L 3/502761* (2013.01); *G01N 15/00* (2013.01); *G01N 27/4473* (2013.01); *G01N 27/44704* (2013.01); *G01N 27/44791* (2013.01);
(Continued)

(58) Field of Classification Search
None
See application file for complete search history.

(56) References Cited

U.S. PATENT DOCUMENTS

2008/0283402 A1  11/2008  Peach

FOREIGN PATENT DOCUMENTS

| JP | 2009262107 A | 11/2009 |
| JP | 2013238463 A | 11/2013 |
| WO | 2014/207618 A1 | 12/2014 |

OTHER PUBLICATIONS

S. K. Amen, et al. "Utilization of graphene electrode in transparent microwell arrays for high throughput cell trapping and lysis", Biosensors and Bioelectronics, 61:p. 625-630, Nov. (Year: 2014).*

* cited by examiner

*Primary Examiner* — J. Christopher Ball
(74) *Attorney, Agent, or Firm* — Harrington & Smith

(57) ABSTRACT

Method, apparatus, and computer program product for a microfluidic channel having a cover opposite its bottom and having electrodes with patterned two-dimensional conducting materials, such as graphene sheets integrated into the top of its bottom. Using the two-dimensional conducting materials, once a fluid sample is applied into the channel, highly localized modulated electric field distributions are generated inside the channel and the fluid sample. This generated field causes the inducing of dielectrophoretic (DEP) forces. These DEP forces are the same or greater than DEP forces that would result using metallic electrodes because of the sharp edges enabled by the two-dimension geometry of the two-dimensional conducting materials. Because of the induced forces, micro/nano-particles in the fluid sample are separated into particles that respond to a negative DEP force and particles that respond to a positive DEP. Microfluidic chips with microfluidic channels can be made using standard semiconductor manufacturing technology.

19 Claims, 9 Drawing Sheets

(51) Int. Cl.
*G01N 35/00* (2006.01)
*G01N 15/00* (2006.01)

(52) U.S. Cl.
CPC . *G01N 35/00029* (2013.01); *G01N 35/00871* (2013.01); *B01L 2200/0652* (2013.01); *B01L 2200/0668* (2013.01); *B01L 2300/023* (2013.01); *B01L 2300/04* (2013.01); *B01L 2300/0627* (2013.01); *B01L 2300/0816* (2013.01); *B01L 2300/0864* (2013.01); *B01L 2300/12* (2013.01); *B01L 2400/0424* (2013.01); *G01N 2015/0053* (2013.01)

PARTICLE MANIPULATION AND TRAPPING IN MICROFLUIDIC DEVICES USING TWO-DIMENSIONAL MATERIAL

TECHNICAL FIELD

This invention relates generally to microfluidic device wherein particles can be manipulated or trapped using two-dimensional conducting materials.

BACKGROUND

This section is intended to provide a background or context to the invention disclosed below. The description herein may include concepts that could be pursued, but are not necessarily ones that have been previously conceived, implemented or described. Therefore, unless otherwise explicitly indicated herein, what is described in this section is not prior art to the description in this application and is not admitted to be prior art by inclusion in this section.

Microfluidic space devices offer benefits as they are in effect miniaturize laboratories with advantages of low-energy, low sample, and low by a receptor consumption; high integration, multiplexing, and compactness; fast results; low cost. Moreover such devices have the potential for applications as research platforms as well as point-of-care devices.

Microfluidics also facilitates touchless manipulation of single cells, organisms, or particles through the exploitation of the "dielectrophoresis" effect. A dielectrophoretic (DEP) force arises from the polarization of otherwise electrically neutral particles or cells when suspended in a non-homogeneous electric field. This polarization occurs due to the imbalanced distribution of bounded charges induced by the electric field, and acts to attract (repel) cells to (from) electric field maxima for positive (negative) dielectrophoresis force, as described in the following equation:

$$F_{DEP}=2\pi R^3 \varepsilon_m CM \quad (1)$$

where
R: Radius
$\varepsilon_m$: permittivity
CM: Claussius-Mossotti Factor

These forces depend not only on the geometrical configuration and excitation scheme of the electric field but also on the dielectric properties of the cell and of its suspending medium, hence can be used for particle discrimination, separation, isolation or concentration, useful for sample processing.

Particle or cell manipulation through dielectrophoresis requires creating an electric field gradient within the sample fluid, which prior to this invention could be done two different ways: (1) with an arrangement planar metallic electrodes integrated in the microfluidic channel, often in direct contact with the fluid containing the particles or cells; or (2) with highly focused laser beams commonly known as Optical Tweezers requiring large and expensive optical equipment.

Integrated electrodes in microfluidic channels can be used with other purposes in addition to generating DEP forces (both positive or negative) such as electrical sensing (impedance, capacitance, etc.), optical illumination and detection, heating mechanism to induce reactions, etc.

Common materials used as metallic electrodes, such as aluminum (Al), gold (Au), platinum (Pt), palladium (Pd), are used in part due to their stability when used in direct contact with the flow at moderate electrical voltages. Integration of metallic electrodes into microfluidic channels is most commonly done on silicon substrates, but it has also been used on glass substrates. They may also be used in plastic substrates. Common thickness of these metallic electrodes is of the order of 50 nm-100 nm. Occasionally a thin (~5 nm) layer of titanium (Ti) is deposited between substrate and electrode to improve adhesion. The topography created by the electrodes on the path of the fluid can interfere with the progression of the flow meniscus, for instance, during filling of the channel, or with the particles suspended in the fluid, causing them to stick to the surface, especially with cells or other biological organisms. Thus, fabrication techniques have been devised to minimize the topography introduced by the integrated electrodes Ex: including one additional etching step to undercut into the substrate surface (ex: silicon oxide) prior to metal deposition. (See: WO 2014/207618 A1 "Microfluidic chip with dielectrophoretic electrodes extending in hydrophilic flow path) This can add complexity to the manufacturing process that needs to be well calibrated to etch a precise depth.

In addition, metallic structures can also impact cell integrity, react with the sample and cause bubbles due to electrolysis at high electric fields. Further challenges with metallic electrodes arise when employing optical detection methods where opaque metallic electrodes can interfere with the image. In addition, metallic electrodes are not flexible to be used on flexible substrates such as polymers, plastic, paper, and are harder to dispose (due to cost, contamination concerns) when used on low cost and disposable substrates.

On the other hand, certain inorganic layered materials (e.g. graphene, $MoS_2$, $WSe_2$, black phosphorus), regular arrays and random networks/thin films made of quasi-one dimensional lattice structures such as organic and inorganic nanotubes/nanowires (e.g. carbon nanotubes, Si nanowires, . . . ) can be used for implementation of similar functionalities as described above for metallic electrodes. Moreover, some are 2D semiconducting materials with the added functionality for gate modulated processes such light emission and detection. In addition, a process exists (see YOR820140381: Microfluidic and nanofluidic chips with application-specific device arrays employing a two-dimensional lattice structure) for transferring a 2-dimensional lattice structure onto a substrate patterned with microchannel topography, and for patterning the 2-dimensional lattice structure afterwards into arbitrary shapes within the microfluidic device.

Transfer is achieved by growing or depositing a 2-dimensional material (e.g. graphene or a carbon nanotube film) on a substrate and to spin-on a layer of e.g. PMMA for transfer (or by dissolving the substrate itself). The 2D material plus PMMA layer system is then deposited on top of the channel system before the PMMA is removed in a final lift-off step. Subsequent patterning of the 2-dimensional lattice is achieved through standard semiconductor fabrication methods. Additional patterning and contacting steps can follow before the final capping or sealing of the channel.

The current invention moves beyond these techniques and materials.

Abbreviations that may be found in the specification and/or the drawing figures are defined below, after the detailed description section.

BRIEF SUMMARY

This section is intended to include examples and is not intended to be limiting.

An example of an embodiment, is a method that comprises a method, comprising applying a fluid sample into a microfluidic channel, wherein the microfluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured; generating highly localized modulated electric field distribution inside the channel and the fluid sample using the two-dimensional conducting materials; based on the generating, inducing DEP forces, wherein the DEP forces are the same or greater than DEP forces that would use metallic electrodes due to the sharp edges enabled by the two-dimension geometry of the two-dimensional conducting materials; and in response to the inducing, separating micro/nano-particles in the fluid sample into particles that respond to a negative DEP force and particles that respond to a positive DEP.

An example of another embodiment of the present invention is an apparatus a microfluidic channel where a fluid sample can be applied into, wherein the microfluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured; and a generator to generate highly localized modulated electric field distribution inside the channel and the fluid sample using the two-dimensional conducting materials, wherein based on said generating, DEP forces are induced, wherein the DEP forces are the same or greater than DEP forces that would use metallic electrodes due to the sharp edges enabled by the two-dimension geometry of the two-dimensional conducting materials, and wherein in response to said inducing, micro/nano-particles in the fluid sample are separated into particles that respond to a negative DEP force and particles that respond to a positive DEP.

In another example of an embodiment of the current invention is a computer program product embodied on a non-transitory computer-readable medium in which a computer program is stored that, when being executed by a computer, would be configured to provide instructions to control or carry out applying a fluid sample into a microfluidic channel, wherein the microfluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured; generating highly localized modulated electric field distribution inside the channel and the fluid sample using the two-dimensional conducting materials; based on the generating, inducing DEP forces, wherein the DEP forces are the same or greater than DEP forces that would use metallic electrodes due to the sharp edges enabled by the two-dimension geometry of the two-dimensional conducting materials; and in response to the inducing, separating micro/nano-particles in the fluid sample into particles that respond to a negative DEP force and particles that respond to a positive DEP.

In another example of an embodiment of the current invention is an apparatus comprising means for accepting an application of a fluid sample into a microfluidic channel, wherein the microfluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured; means for generating a highly localized modulated electric field distributions inside the channel and the fluid sample using the two-dimensional conducting materials; based on the generating, means for inducing DEP forces, wherein the DEP forces are the same or greater than DEP forces that would use metallic electrodes due to the sharp edges enabled by the two-dimension geometry of the two-dimensional conducting materials; in response to the inducing, means for separating micro/nano-particles in the fluid sample into particles that respond to a negative DEP force and particles that respond to a positive DEP.

DETAILED DESCRIPTION OF THE DRAWINGS

In order to overcome some of the disadvantages of the current state of affairs, exemplary embodiments of the current invention look to use novel 2-dimensional conducting materials such as patterned graphene sheets in place of thick metallic electrodes integrated in microfluidic channels for generation of highly localized modulated electric field distributions inside the channel and the fluid sample. Sheets of graphene of size compatible with microfluidic chips can be fabricated and patterned using standard semiconductor manufacturing technology into any arbitrary shape inside and outside the channel to ensure electrical contact, such that these 2D electrodes can create the same or improved electric field modulation locally by the electrode that induces the same or more intense DEP forces due to the sharp edges enabled by the 2D geometry.

The word "exemplary" as used herein means "serving as an example, instance, or illustration." Any embodiment described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

Figure 1A:
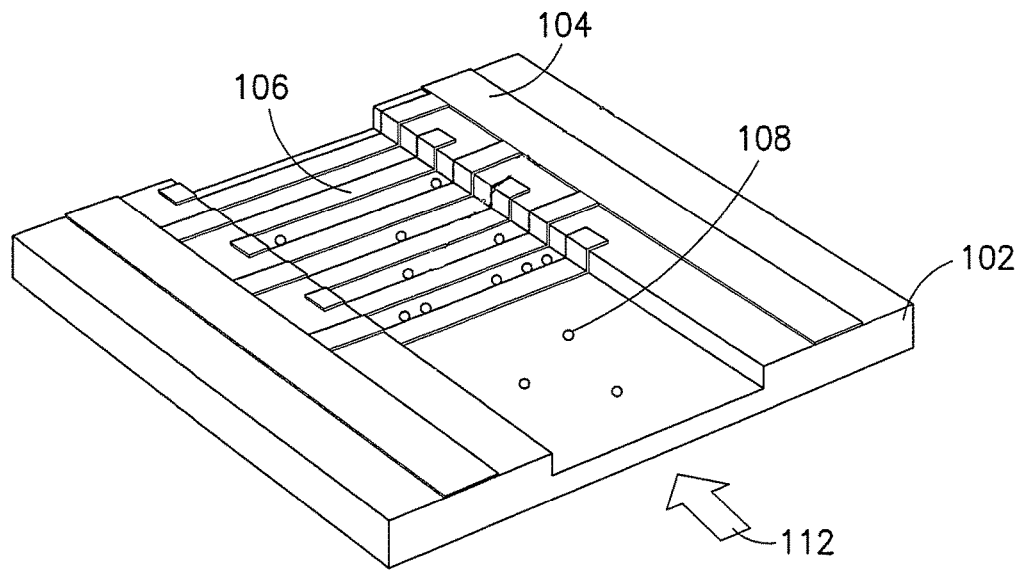
FIGS. 1A and 1B are depictions of the prior art and an example of a physical embodiment of the proposed invention, respectively.
Figure 1B:
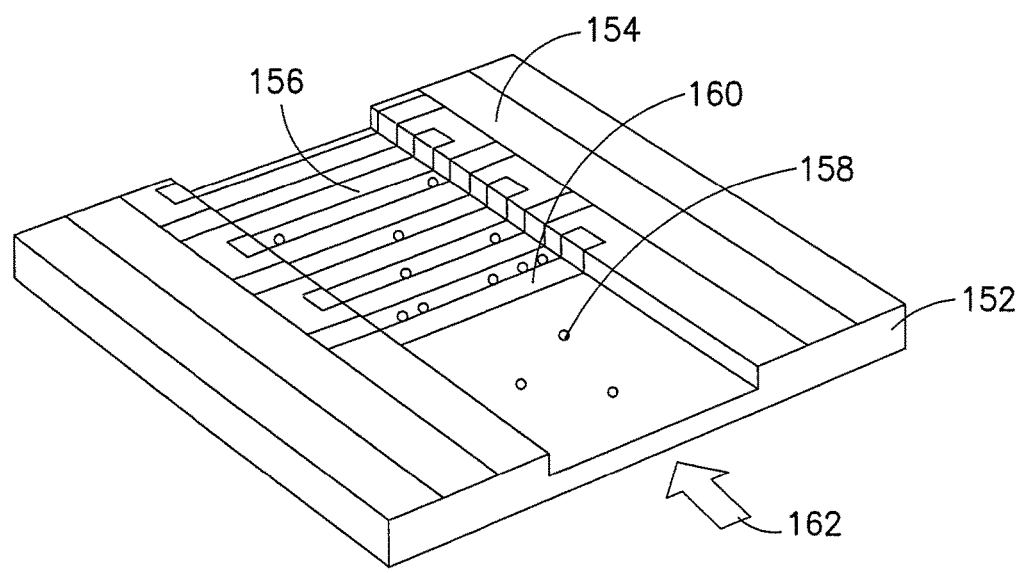

Turning to FIGS. 1A and 1B, which are depictions of the prior art and an example of a physical embodiment of the proposed invention, respectively.

FIG. 1A shows microchip block 102 which comprises flow channel 112 and thick metallic electrodes 104 and 106. Electrodes 104 run alongside channel 112 while electrode 106 are contained within the flow channel 112. Flow channel 112 is a microfluidic flow channel and micro/nano particles 108 enter the microfluidic channel 112 and proceed then through the microfluidic channel 112 between electrodes 106.

An exemplary physical embodiment of the proposed invention can be represented in FIG. 1B where microchip block 152 comprises flow channel 162 and two-dimensional graphene 154 and 156 where the graphene structure 154 is outside of the channel connecting to the two-dimensional graphene 156 within microfluidic flow channel 162. Micro/nano particles 158 proceed through microfluidic flow channel 162 and then are separated via two-dimensional graphene 156.

As noted herein, when using two-dimensional graphene electrodes for inducing either positive or negative DEP forces that act over particles 160 flowing in the fluid (not numbered), an optimum balance of forces needs to be achieved in order to produce the desired effect such as trapping, guiding, discriminating, etc.

The main forces in different directions expected to be present in the microchannel with active electrodes are: Positive or negative DEP forces (depending on material properties); Hydrodynamic drag force; Sedimentation forces; Electro-osmotic flow forces; Electrophoretic forces (charged particles); Brownian motion (nano particles). The positive or negative DEP forces and the hydrodynamic drag force are usually the most relevant.

Without in any way limiting the scope, interpretation, or application of the claims appearing below certain design details used in the creation of this invention included common voltage configurations of AC signal @ 1 MHz to 100 MHz; sinusoidal, square or triangular signal; and voltage 1 Vpp to 20 Vpp.

Without in any way limiting the scope, interpretation, or application of the claims appearing below certain design details used in the creation of this invention included common channel dimensions as follows: Width of 100-500 µm; Height of 10-100 µm; Electrode/gap widths of 5-50 µm; Common thickness of 2D materials (graphene electrodes) for Single layer intrinsic thickness it was 0.3 nm and for Multilayer thickness it was up to 10 nm.

Without in any way limiting the scope, interpretation, or application of the claims appearing below certain design details used in the creation of this invention included the common properties of metallic electrodes were thickness of 50 nm-100 nm and using materials such as aluminum (Al), gold (Au), platinum (Pt), palladium (Pd).

Without in any way limiting the scope, interpretation, or application of the claims appearing below certain design details used in the creation of this invention included the properties of other materials as follows: dielectric layers of 1 nm to 1 µm; transparent cover layer thickness, materials such as Dry Film Resist (5 µm-50 µm), PDMS (0.2 mm-3 mm), and PMMA (0.5 mm-5 mm); and silicon oxide thickness of ~200 nm-500 nm.

Without in any way limiting the scope, interpretation, or application of the claims appearing below, an advantage or technical effect of one or more of the exemplary embodiments disclosed herein is that the reduced topography of graphene conductive sheets help produce more uniform, more localized and stronger DEP force traps around the edges. Furthermore, another technical effect of one or more of the examples of embodiments disclosed herein is that the present invention is particularly advantageous when using the 2D electrodes for applications involving positive DEP that pulls particles towards electrode edges, either for trapping or to discriminate between particles that exhibit positive vs negative DEP responses.

Another technical effect of one or more of the exemplary embodiments disclosed herein is that transparent electrodes improve optical/fluorescent detection since it does not interfere with the image and enables detection from the substrate side.

Another technical effect of one or more of the exemplary embodiments disclosed herein is that, alternatively, electrodes can also be used for electrical detection such as impedimetric measurements with potentially higher sensitivity.

Another technical effect of one or more of the exemplary embodiments disclosed herein is that this invention uses graphene sheets which are also flexible, thus can be used on flexible substrates making it compatible with low cost substrates such as plastic or paper.

Another technical effect of one or more of the exemplary embodiments disclosed herein is that graphene consists of pure carbon and is thus biodegradable, making it easier to dispose and readily biocompatible.

Another technical effect of one or more of the exemplary embodiments disclosed herein is that this invention is also less corrosive, likely improving the lifetime of the device.

Figure 2A:
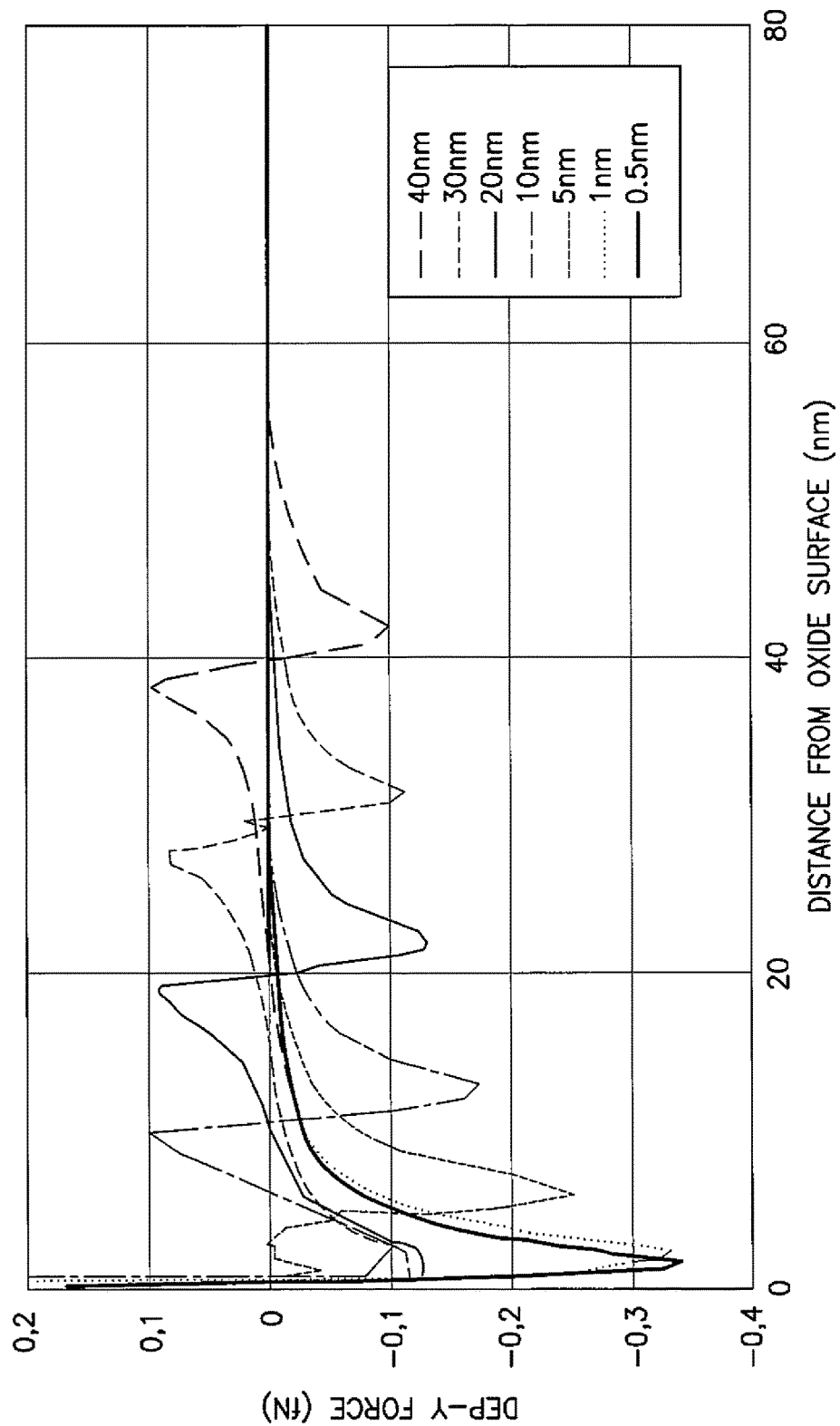
FIG. 2A is a graphical representation of an exemplary advantage of using the two-dimensional graph electrodes rather than the conventional metallic electrodes which have a greater height to them.

Another technical effect of one or more of the exemplary embodiments disclosed herein is that this invention provides higher flexibility with electrode design, size (~100 nm), and topology (curved surfaces), than with current fabrication methods used in micro fluidics devices FIG. 2A is a graphical representation of an exemplary advantage of using the two-dimensional graph electrodes rather than the conventional metallic electrodes which have a greater height to them. The plot displays the component of the DEP force in the direction perpendicular to the silicon oxide surface, referred to as DEP-Y force and measured in fempto Newtons (fN), as computed by solving Maxwell equations using the Finite Element Method. The sign of the force is related to the direction in which a positive-DEP force is being experienced by a particle, with a negative sign representing a force in the negative Y direction and a positive sign representing a force in the positive Y direction. For a given electrode thickness, FIG. 2 shows how the force is stronger in the vicinity of the electrode edge, with its position measured from the oxide surface, and the direction of the force switching signs along the height of the electrode. As the electrode thickness decreases it can be seen in FIG. 2 that the magnitude of the force increases, with fewer oscillations of the sign. Thus, a thinner electrode produces a more localized and stronger pulling force in the direction of the electrode edge. As such, the observer can see a marked improvement in the magnitude of the DEP force with the nearly flat profile of the graphene electrodes as opposed to electrodes made out of traditional metals.

Figure 2B:
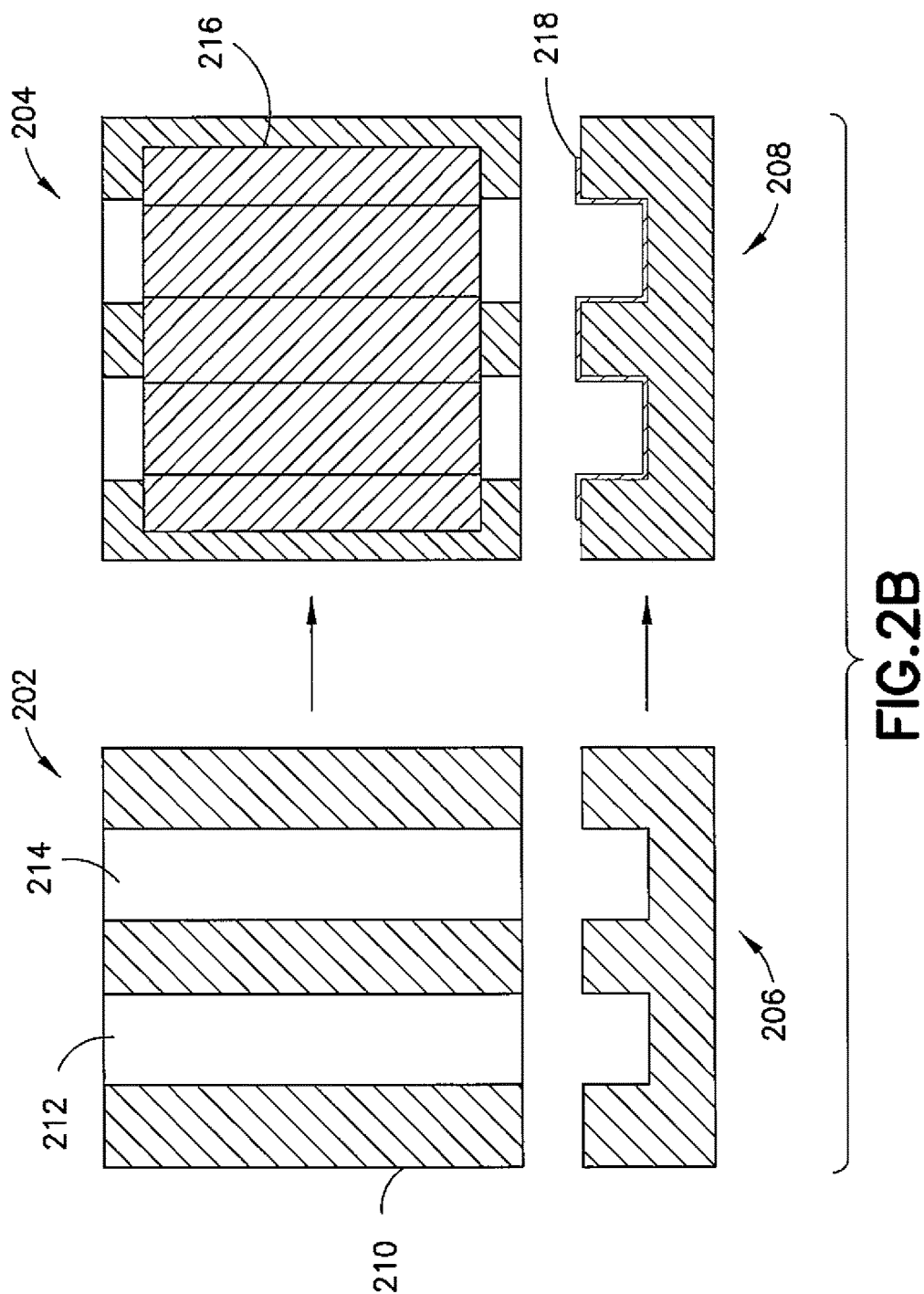
FIG. 2B is a block diagram representation of the transfer of a 2-dimensional lattice structure onto a substrate with fluidic channels.

FIG. 2B is a block diagram representation of the transfer of a 2-dimensional lattice structure onto a substrate with fluidic channels. The diagram consists of top view 202 with its corresponding cross-sectional view 206 and top view 204 with its corresponding cross-sectional view 208. In top view 202, it can be seen that the substrate 210 is showing to microfluidic channels 212 and 214. Top view 204 shows the two dimensional lattice structure 216 over the fluidic channels on the substrate. This same two-dimensional lattice structure on top of the substrate can be seen in cross-sectional view 208 as structure 218.

Figure 2C:
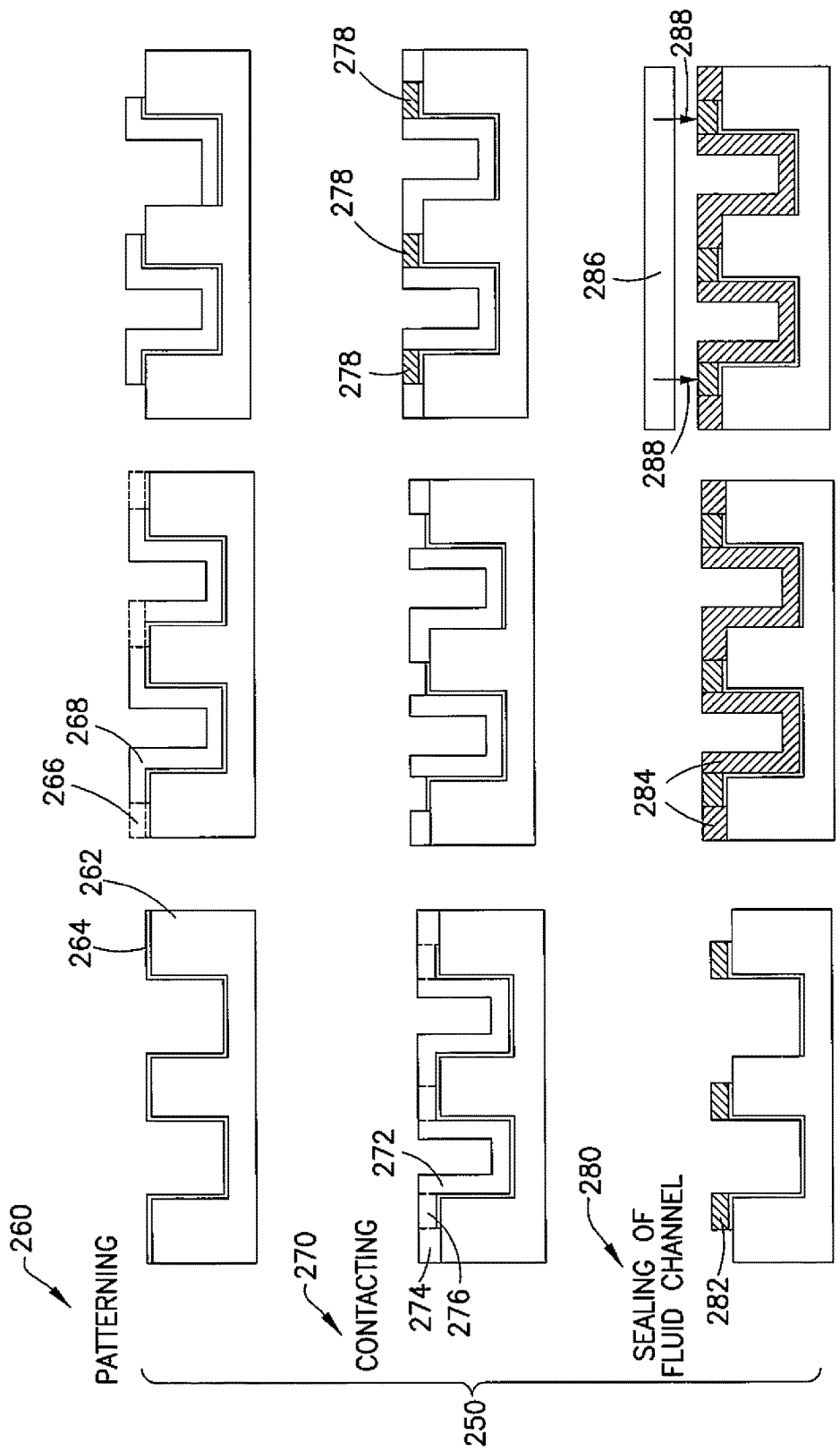
FIG. 2C is a first exemplary structure according to an embodiment of the present disclosure.

Referring to FIG. 2C creating a first exemplary structure according to an embodiment of the present disclosure 250 includes a patterning process 260 of a graphene layer 264 on top of a substrate 262. The substrate 262 can include a conductive material, an insulator material, a semiconductor material, or any solid material provided that the substrate 262 can provide structural support to layers to be subsequently formed. The graphene layer 264 is patterned by applying a negative tone (e.g. HSQ) resist layer that is exposed by a suitable method (electron beam lithography, photolithography). Exposed resist regions 268 will remain while unexposed resist regions 266 will dissolve upon development of the resist layer. In a next step exposed regions of the graphene layer are etched by for example an oxygen plasma step.

This is followed by a contacting process 270 to interface the graphene layer 264. The graphene layer 264 is patterned by applying a positive tone resist (e.g. PMMA) layer that is exposed by a suitable method (electron beam lithography, photolithography). Unexposed resist regions 272, 274 will remain while unexposed resist regions 276 will dissolve upon development of the resist layer. A conductive material 278 is anisotropically deposited in the openings and over the mask layer 272, 274 in a direction perpendicular to the top surface of the graphene layer 264. A portion of the conductive material deposited in the opening forms a contact electrodes 282.

The overlying conductive material layer 274 includes an elemental metal, an alloy of at least two elemental metals, a conductive metallic nitride, a conductive metallic carbide, a doped semiconductor material, an alloy thereof, and/or a stack thereof. The materials that can be employed are but not limited to, Pd, Pt, Ni, Au, Ag, Cu, Al, Ti, Ta, W, TiN, TaN, WN, TiC, TaC, WC, doped silicon, an alloy thereof, and a stack thereof. The conductive material 274 of the contact electrodes 282 can be deposited, for example, by vacuum evaporation, physical vapor deposition, or a combination thereof.

In a last process 280 the device is capped by a depositing a dielectric material 284 like for example $SiO_2$, $SiN_x$, and $Al_2O_3$.

The dielectric material 284 can be formed, for example, by chemical vapor deposition, physical vapor deposition, vacuum evaporation or evaporation at subatomic pressure, atomic layer deposition, spin coating, or a combination thereof.

The whole device is then sealed by top substrate 286 like for example glass or silicon that has vias 288 providing access to the contact electrodes 282.

Figure 3:
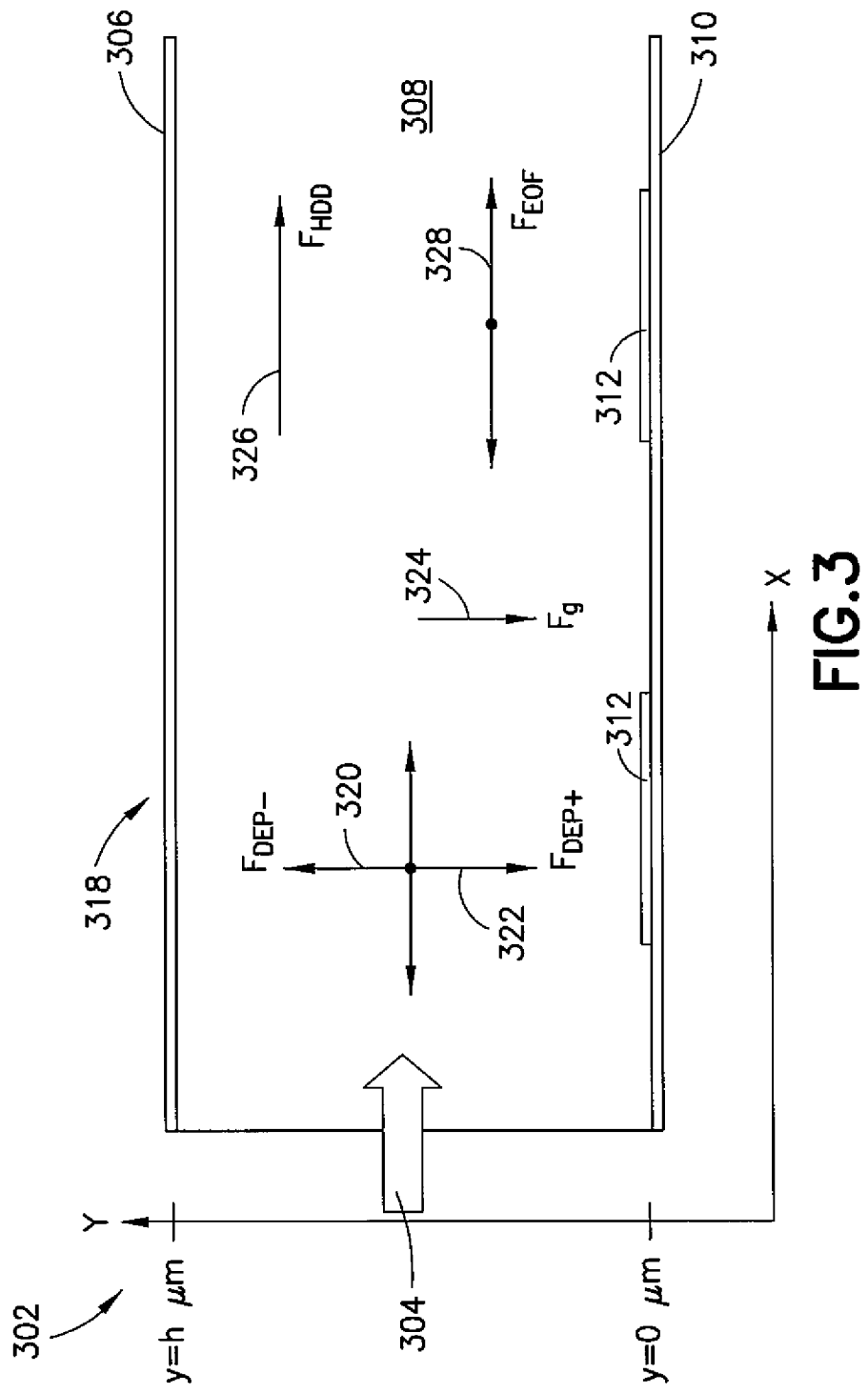
FIG. 3 superimposes graph on a physical representation of an exemplary embodiment of the invention.

Turning now to FIG. 3 which superimposes graph 302 on a physical representation of an exemplary embodiment of the invention 318. Regarding graph 302, the y-axis represents the distance within the microfluidic channel 308 between the cover 306 and the substrate 310. Within exemplary physical embodiment 318, are shown a number of forces that act upon the particles as they flow between cover 306 and substrate 310 through microfluidic channel 308. Positive DEP force 322 and negative DEP force 320 can be seen in relation to graphene electrodes 312. Components of the DEP force acting parallel to the electrodes surface and, in this case, along the direction of the fluid flow exist. While sedimentation force 324 works to pull the micro/nanoparticles toward the graphene electrodes 312, the hydrodynamic drag force 326 of the micro/nano particles moving through microfluidic channel 308 is shown in the same direction as particle flow 304. However, electro-osmotic flow force 328 can work in conjunction with or against the direction of particle flow 304 through microfluidic channel 308.

Without in any way limiting the scope, interpretation, or application of the claims appearing below, three embodiments are presented, the first of which involves Pos-DEP vs Neg-DEP Discrimination.

In a first nonlimiting embodiment, Pos-DEP vs Neg-DEP Discrimination, the stronger force locally to the 2-dimensional electrode edge predicted by simulations will pull particles exhibiting a pos-DEP response stronger than thicker electrodes. This would improve the discrimination between particles showing positive and negative DEP behavior. Moreover, transparent electrodes would not interfere with the analysis of the pos-DEP particles trapped at the electrodes.

For example, pos-DEP particles could be trapped at the electrode edges while the neg-DEP particles flow unaffected along the channel. This assumes that the channel design and voltage applied to the electrodes has been tuned so that the drag of the fluid is stronger than the neg-DEP force experienced by the corresponding set of particles with neg-DEP response, while the pos-DEP force experienced by the corresponding set with pos-DEP response is stronger than the drag.

For example, malaria infected red blood cells have lost most ionic content and show a neg-DEP response while healthy red blood cells' membrane maintains the ions inside the cell and show a pos-DEP response.

In order for particles responding to pos-DEP to be trapped at the electrode edges while particles responding to neg-DEP flow unaffected along the channel, the following design constraints need to be satisfied:

For particles responding to neg-DEP:

$$F_{DEP_Y}|_{y>0,\forall x} > F_g|_{y>0,\forall x} \tag{2}$$

where $F_g$ is the force of gravity. To guarantee electrode-induced particle levitation up to a plane y=(h−R) high, with R=particle radius, and $$(F_{DEP_X} + F_{EOF_X})|_{\substack{y=h-R,\\ \forall x}} < F_{HDD_X}|_{\substack{y=h-R,\\ \forall x}} \tag{3}$$

to guarantee particles flow away with the fluid.

For particles responding to pos-DEP:

$$F_{DEP_X}|_{\substack{y=0,\\ x=electrode\\ edges}} > (F_{HDD_X} + F_{EOF_X})|_{\substack{y=0,\\ x=electrode\\ edges}} \tag{4}$$

to guarantee particles are trapped against the flow. Where the forces depend on various system and user defined parameters, that is:

For Hydrodynamic drag force, Flow speed ($\vec{v}$), Fluid viscosity ($\eta$), Particle size (R):

$$\vec{F}_{HDD} = 6\pi\eta R \vec{v} \qquad (5)$$

For Electrode layout and Voltage-dependent electric field distribution (E), Materials permittivity (ε), Particle size (R)

$$\vec{F}_{DEP} = 2\pi\varepsilon_m R^3 CM\nabla|E|^2 \qquad (6)$$

Materials density (ρ), Gravitational constant ($\vec{g}$), Particle size (R):

$$\vec{F}_g = \frac{4}{3}\pi R^3 (\rho_p - \rho_m)\vec{g} \qquad (7)$$

And the electro-osmotic flow forces.

Hence for a given set of system parameters (fixed during operation), and assuming the geometry of the channel as well as the speed of the flow are also fixed, the user can modulate the voltage applied to the electrodes in between:

$$V_{min} < V_{operation} < V_{max} \qquad (8), \text{ where}$$

$V_{min}$: Minimum voltage that guarantees particles responding to pos-DEP to be trapped at the electrode edges on the bottom of the channel (referring to equation (3), above)

$V_{min}$: Maximum voltage to be applied to the electrodes before particles responding to neg-DEP start experiencing a DEP force larger than the drag of the fluid and, therefore become trapped (referring to equation (4), above)

Sedimentation and EOF (Electro-osmotic flow) forces are often too weak and can be assumed negligible.

The electrode layout can also be adjusted in conjunction with the channel geometry during the device design stage to better achieve the desired effect. Common electrode width dimensions are of the order of the size of the particles intended for manipulation, i.e. R.

Figure 4:
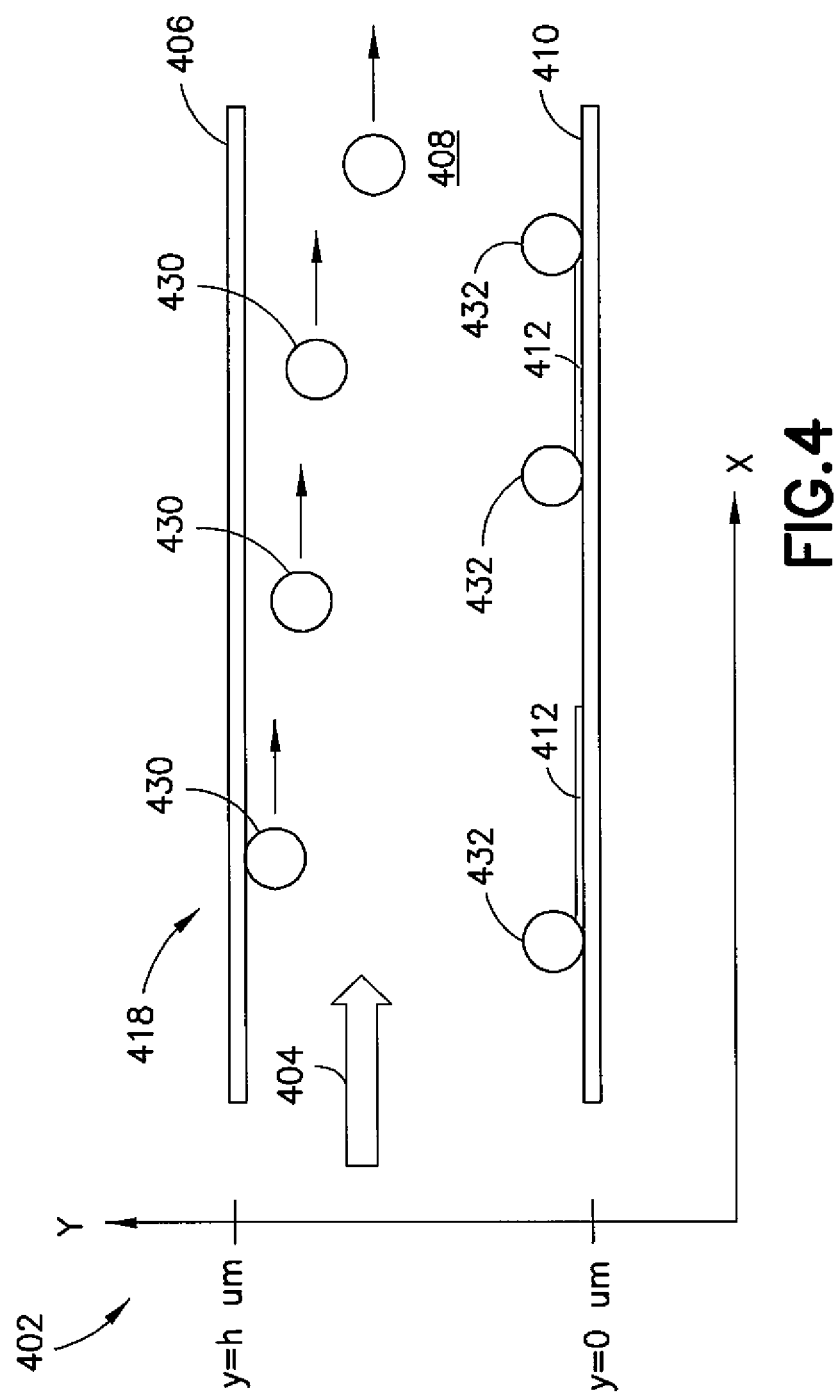
FIG. 4 is a representation of an example of the first embodiment with the graph superimposed upon it.

FIG. 4 is a representation of an example of this first embodiment 418 with the graph 402 superimposed upon it. As in the previous figure, we have micro fluidic channel 408 which has cover 406 and substrate 410 upon which graphing of electrodes 412 reside. The flow of the micro/nanoparticles through microfluidic channel 408 is in the direction indicated by flow 404. Within that flow 404 of micro/nanoparticles are two sets of particles responding to the negative DEP force, namely particles or cells 430, and those particles or cells responding to the positive DEP force 432.

In a second nonlimiting embodiment, Particle Trapping and Detection with DEP, conventional negative DEP levitation and trapping on top of the electrode and under the cover can be achieved using 2-dimensional electrodes just as well as with metallic thicker electrodes. This assumes that the channel and voltage have been designed such that the neg-DEP force experienced by the particle is stronger than the hydrodynamic drag and therefore the particles remain trapped in place.

Transparent 2-dimensional electrodes in combination with transparent substrates enable back illumination and image capture from the substrate side. Many optical detection systems rely on back illumination and detection (from the substrate side) such as inverted microscopes or require the image to be captured from the substrate side not to interfere with sample deposition and processing. In those cases, the use of opaque metallic electrodes, even with transparent substrates, can interfere with image capture.

In order to trap particles that only respond to negative DEP (i.e. are repelled away from electrodes) and are, therefore levitated over the electrodes up to the cover, the force applied by the electrodes needs to be strong enough to overcome the drag of the flow. Hence the design equations should satisfy:

$$F_{DEP_Y}|_{y>0,\forall x} > F_g|_{y>0,\forall x} \qquad (9)$$

to guarantee electrode-induced particle levitation up to a plane y=(h−R) high, with R=particle radius, and $$F_{DEP_X}|_{\substack{y=h-R, \\ x=electrode \\ edges}} > (F_{HDD_X} + F_{EOF_X})|_{\substack{y=h-R, \\ x=electrode \\ edges}} \qquad (10)$$

to guarantee particles are trapped against the flow.

So similarly to embodiment 1, for a certain set of system parameters, channel and electrode geometry and flow speed, the voltage applied to the electrodes need to produce a DEP force capable of overcoming the drag of the fluid to securely trap particles levitating over the electrodes.

$$V_{operation} > V_{min} \qquad (11)$$

This voltage, however, should remain within safe limits to avoid damaging biological reagents (typ. 20 Vpp).

Figure 5:
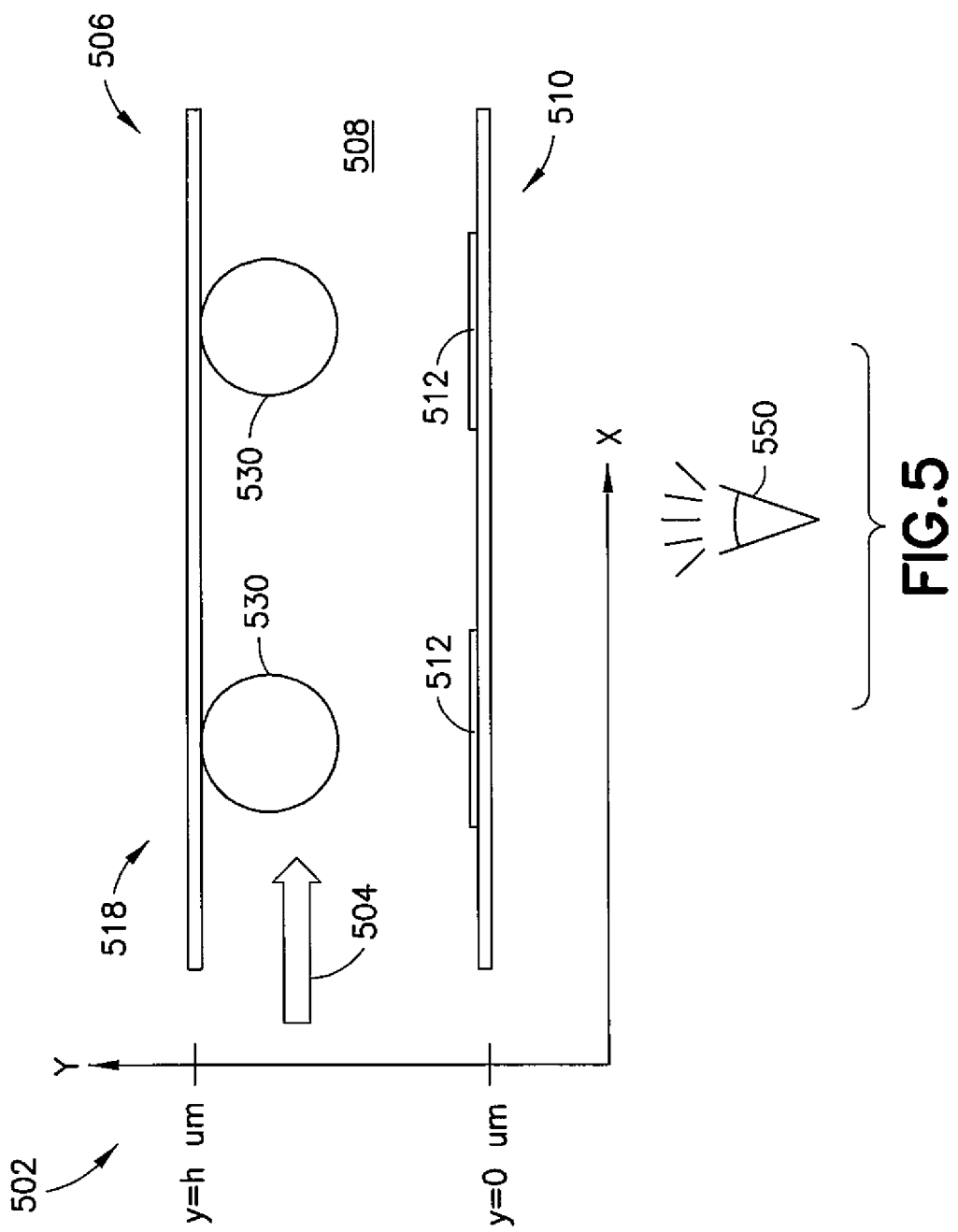
FIG. 5 depicts an example of a representation of a second embodiment with the physical structure having a graph superimposed upon it.

An example of a representation of this second embodiment is depicted in FIG. 5, wherein again we have the physical structure of an exemplary embodiment 518 with graph 502 superimposed upon it. Once again we have cover 506 and substrate 510 and closing microfluidic channel 508 where the graphene electrodes 512 are once again in contact with substrate 510. However, in examples of this particular embodiment, the substrate 510 is transparent allowing optical access 550 from the substrate side 510 of the embodiment. Through microfluidic channel 508 again there is a flow 504 of particles which respond to negative DEP forces, those particles or cells labeled in the diagram as 530.

Figure 6A:
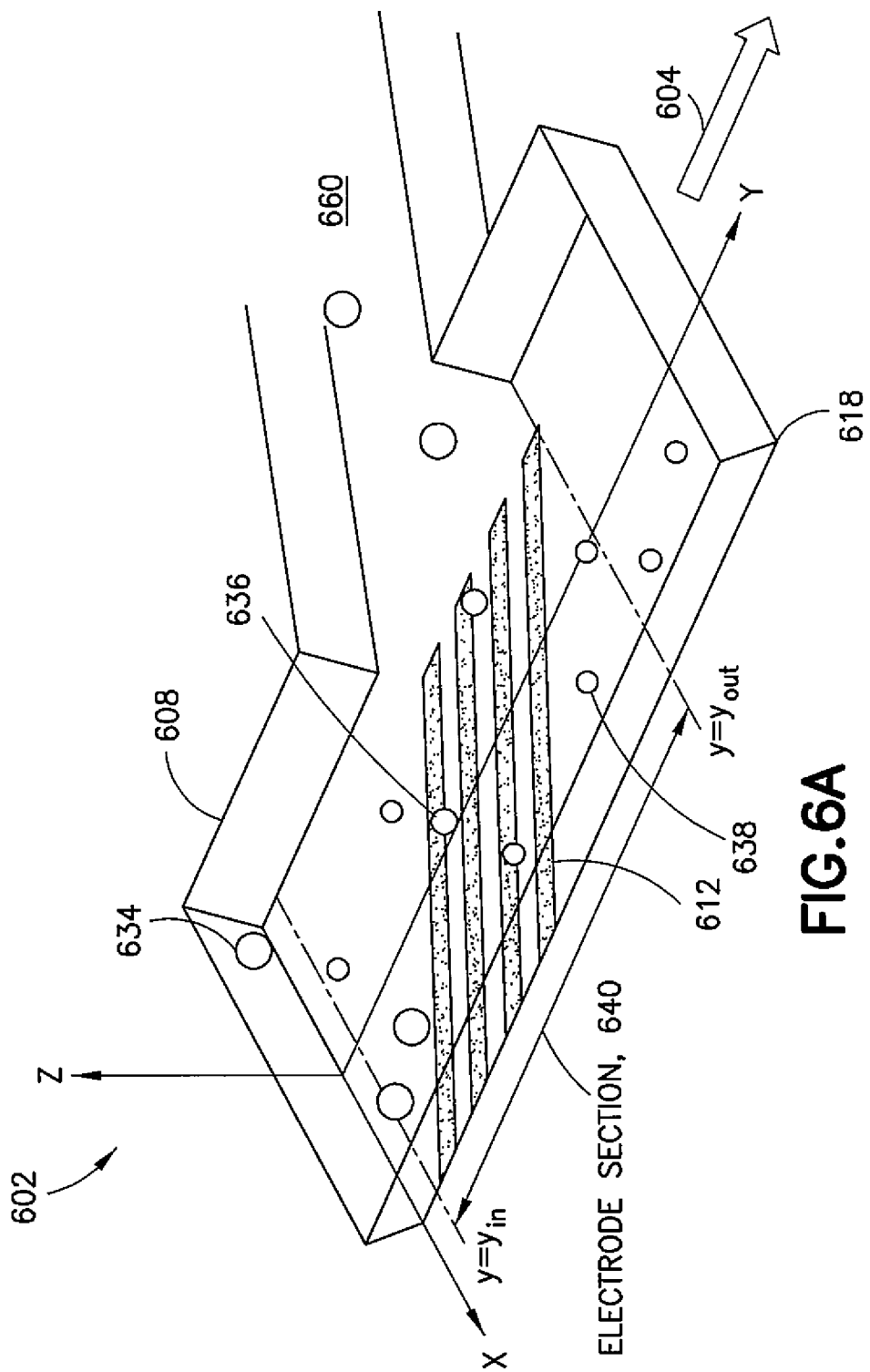
FIG. 6A shows a third nonlimiting embodiment with a graph superimposed on it and FIG. 6B shows a force diagram based on the graph of FIG. 6A.

In a third nonlimiting embodiment, Particle Manipulation with Neg-DEP, negative DEP can be used to control the movement of particles inside the microchannel without trapping them such as the slanted electrodes in FIG. 6A. For example, slanted electrodes can be used to push larger particles into side channels while letting smaller particles pass unaffected. This same functionality can be achieved by replacing thick metallic electrodes with 2-dimensional graphene electrodes with the additional advantages listed herein.

In this third nonlimiting embodiment, all particles respond only to negative DEP but they are of different size or even material properties. The DEP force depends strongly on the particle size (through $R^3$) and the particle material properties (through the Clausius-Mossotti (CM) factor). Assuming for simplicity that the particles only differ in size, then:

$$\text{if } R^A > R^B \text{ then } F_{DEP}^A > F_{DEP}^B \qquad (12)$$

and particles can be discriminated based on their size according to the following design equations:

$$z = 0 \text{ channel bottom} \qquad (13)$$

$$z = h \text{ channel top} \qquad (14)$$

$$x \in \left(-\frac{W}{2}, \frac{W}{2}\right) \text{ Within channel} \qquad (15)$$

For all particles within the electrode section:

$$F_{DEP_Z}^{A,B}\Big|_{\substack{z>0,\forall x \\ y_{in}<y<y_{out}}} > F_g^{A,B}\Big|_{\substack{z>0,\forall x \\ y_{in}<y<y_{out}}} \qquad (16)$$

to guarantee electrode-induced particle levitation.

For particles with radius $R^B$, the tangential components of the force on a plane at a height $z=h-R^B$ satisfy:

$$F_{DEP_X}^{B}\Big|_{\substack{z=h-R^B, \\ \forall x \\ \forall y}} < F_{HDD_X}^{B}\Big|_{\substack{z=h-R^B, \\ \forall x \\ \forall y}} \qquad (17)$$

and $$F_{DEP_Y}^{B}\Big|_{\substack{z=h-R^B, \\ \forall x \\ \forall y}} < F_{HDD_Y}^{B}\Big|_{\substack{z=h-R^B, \\ \forall x \\ \forall y}} \qquad (18)$$

to guarantee that the smaller particles are unaffected by the DEP force and flow away with the fluid along the main channel at all times. (for simplicity, electro-osmotic flow is assumed negligible).

For particles with radius $R^A$, the tangential components of the force at the plane $z=h-R^A$ need to satisfy:

$$F_{DEP_Y}^{A}\Big|_{\substack{z=h-R^A, \\ \forall x \\ y_{in}<y<y_{out}}} < F_{HDD_Y}^{A}\Big|_{\substack{z=h-R^A, \\ \forall x \\ y_{in}<y<y_{out}}} \qquad (19)$$

to guarantee that the larger particles move forward along the direction of the main channel and do not become trapped and $$F_{DEP_X}^{A}\Big|_{\substack{z=h-R^A, \\ \forall x \\ y_{in}<y<y_{out}}} < F_{HDD_X}^{A}\Big|_{\substack{z=h-R^A, \\ \forall x \\ y_{in}<y<y_{out}}} \qquad (20)$$

to guarantee that the larger particles move toward the side channel in the desired direction as designed by the electrode orientation.

Arrangements for examples of this third particular embodiment are shown in FIG. 6A wherein a three-dimensional view of the exemplary embodiment 618 is superimposed over three-dimensional graph 602 where the x-axis runs along the width of the microfluidic channel 608, y-axis running along the length of microfluidic channel 608 in the direction of flow 604, and the z-axis indicating the distance from the top to the bottom of microfluidic channel 608.

Additionally in this diagram are side channel 660 through which separated particles exit as a result of the particles interacting with graphene electrodes 612. As can be seen from the diagram particles herein are of various sizes from the largest 634 through medium sized particles 636 to the smallest particles 638. These various particles will be segregated via graphene electrodes 612 which neighbor the in the space within the channel between $y_{in}$ and $y_{out}$, labeled as the Electrode section 640.

Based on the superimposed graph 602 in FIG. 6A, graph 634 in FIG. GB shows electrode 614 of electrodes 612 with total force 670 and DEP force 672 along with hydrodynamic force 674 in relation to the electrode 614.

Figure 7:
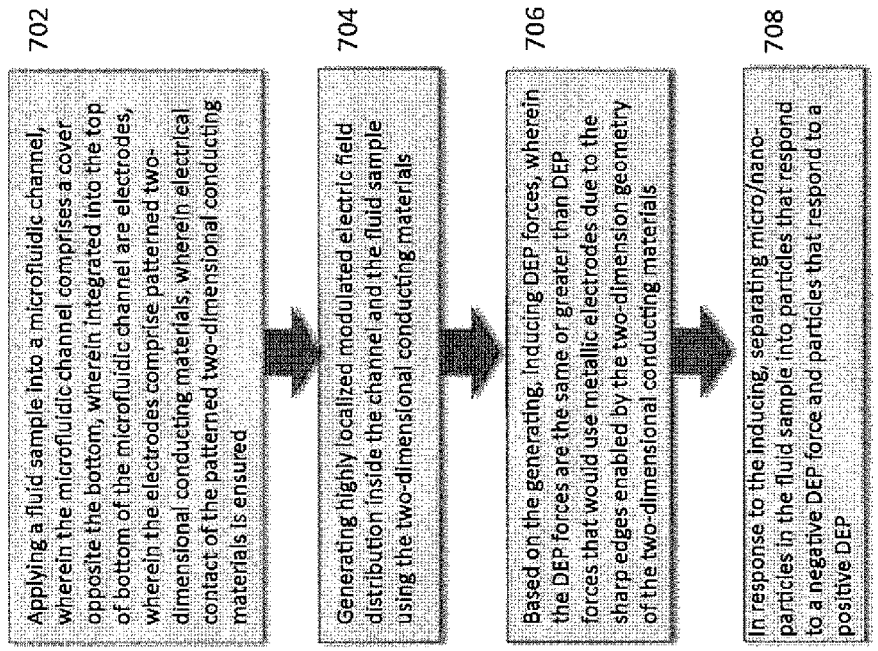
FIG. 7 is a logic flow diagram for particle manipulation and trapping in microfluidic devices using two-dimensional material, and illustrates the operation of an exemplary method, a result of execution of computer program instructions embodied on a computer readable memory, functions performed by logic implemented in hardware, and/or interconnected means for performing functions in accordance with exemplary embodiments.
Figure 6B:
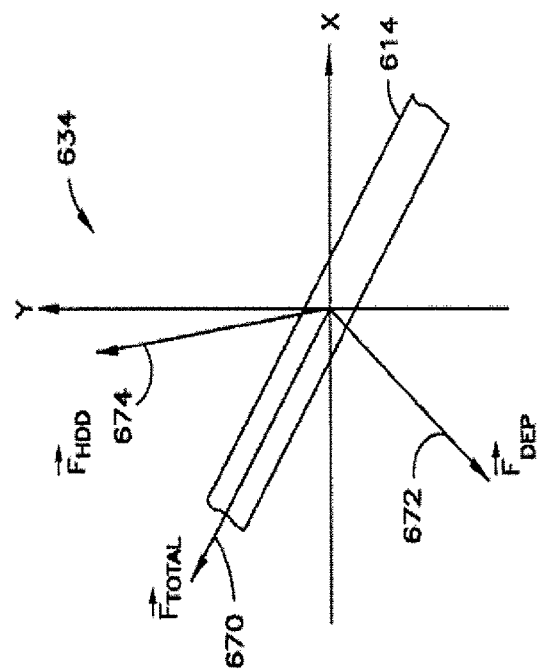

FIG. 7 is a logic flow diagram for particle manipulation and trapping in microfluidic devices using two-dimensional material, and illustrates the operation of an exemplary method, a result of execution of computer program instructions embodied on a computer readable memory, functions performed by logic implemented in hardware, and/or interconnected means for performing functions in accordance with exemplary embodiments.

Item 702 represents applying a fluid sample into a microfluidic channel, wherein the microfluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured. Item 704 represents generating highly localized modulated electric field distribution inside the channel and the fluid sample using the two-dimensional conducting materials. Item 706 represents, based on the generating, inducing DEP forces, wherein the DEP forces are the same or greater than DEP forces that would use metallic electrodes due to the sharp edges enabled by the two-dimension geometry of the two-dimensional conducting materials. Item 702 represents, in response to the inducing, separating micro/nano-particles in the fluid sample into particles that respond to a negative DEP force and particles that respond to a positive DEP.

Embodiments herein may be implemented in software (executed by one or more processors), hardware (e.g., an application specific integrated circuit), or a combination of software and hardware. In an example of an embodiment, the software (e.g., application logic, an instruction set) is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer, with one example of a computer described and depicted, e.g., in FIG. 1. A computer-readable medium may comprise a computer-readable storage medium (e.g., 104, 134 or other device) that may be any media or means that can contain, store, and/or transport the instructions for use by or in connection with an instruction execution system, apparatus, or device, such as a computer. A computer-readable storage medium does not comprise propagating signals.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

An example of an embodiment, which can be referred to as item 1, is a method that comprises a method, comprising applying a fluid sample into a microfluidic channel, wherein the microfluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured; generating highly localized modulated electric field distribution inside the channel and the fluid sample using the two-dimensional conducting materials; based on the generating, inducing DEP forces, wherein the DEP forces are the same or greater than DEP forces that would use metallic electrodes due to the sharp edges enabled by the two-dimension geometry of the two-dimensional conducting materials; and in response to the inducing, separating micro/nano-particles in the fluid sample into particles that respond to a negative DEP force and particles that respond to a positive DEP.

An example of a further embodiment, which can be referred to as item 2, is the method of item 1 wherein the two-dimensional conducting materials comprise graphene sheets.

An example of a further embodiment, which can be referred to as item 3, is the method of item 1, wherein a microfluidic chip comprises the microfluidic channel.

An example of a further embodiment, which can be referred to as item 4, is the method of item 3 wherein microfluidic chips can be fabricated and patterned using standard semiconductor manufacturing technology.

An example of a further embodiment, which can be referred to as item 5, is the method of item 3 where the microfluidic chip further comprises a generator for the generating.

An example of a further embodiment, which can be referred to as item 6, is the method of item 1, wherein the two-dimensional conducting materials can be patterned into any arbitrary shape inside and outside the channel, wherein the two-dimensional conducting materials acting as two-dimensional electrodes create a same or improved electric field modulation locally than metallic electrodes.

An example of a further embodiment, which can be referred to as item 7, is the method of item 1, further comprising designing the channel and voltage for the negative DEP force experienced by the particle to be stronger than the hydrodynamic drag; trapping particles in place with conventional negative DEP levitation on top of the electrode and under the cover; and detecting the trapped particles.

An example of a further embodiment, which can be referred to as item 8, is the method of item 1, further comprising, in response to the particles interacting with the electrodes, separating particles via side channels by size.

An example of a further embodiment, which can be referred to as item 9, is the method of item 1, further comprising determining, in response to the separating, numbers of particles that respond to a negative DEP force and of particles that respond to a positive DEP, wherein the determining can be done by at least one of a micro fluidic chip comprising the microfluidic channel and a microprocessor, and a device connecting to a microfluidic chip comprising the microfluidic channel, wherein the connecting can be a physical connection or a wireless connection.

An example of a further embodiment, which can be referred to as item 10, is the method of item 9, further comprising outputting results of the determining.

An example of another embodiment of the present invention, which can be referred to as item 11, is an apparatus a microfluidic channel where a fluid sample can be applied into, wherein the microfluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured; and a generator to generate highly localized modulated electric field distribution inside the channel and the fluid sample using the two-dimensional conducting materials, wherein based on said generating, DEP forces are induced, wherein the DEP forces are the same or greater than DEP forces that would use metallic electrodes due to the sharp edges enabled by the two-dimension geometry of the two-dimensional conducting materials, and wherein in response to said inducing, micro/nano-particles in the fluid sample are separated into particles that respond to a negative DEP force and particles that respond to a positive DEP.

An example of a further embodiment, which can be referred to as item 12, is the apparatus of item 11, wherein the two-dimensional conducting materials comprise graphene sheets.

An example of a further embodiment, which can be referred to as item 13, is the apparatus of item 11, wherein a microfluidic chip comprises the apparatus.

An example of a further embodiment, which can be referred to as item 14, is the apparatus of item 13, wherein microfluidic chips can be fabricated and patterned using standard semiconductor manufacturing technology.

An example of a further embodiment, which can be referred to as item 15, is the apparatus of item 11, further comprising at least one processor; and at least one memory including computer program code, wherein the at least one processor, in response to execution of the computer program code, is configured to cause the apparatus to control or perform at least one of: depositing the fluid sample into the microfluidic channel; generating the highly localized field distribution; and in response said separating of particles, calculating a number of particles separated.

An example of a further embodiment, which can be referred to as item 16, is the apparatus of item 11, wherein the two-dimensional conducting materials can be patterned into any arbitrary shape inside and outside the channel, wherein the two-dimensional conducting materials acting as two-dimensional electrodes create a same or improved electric field modulation locally than metallic electrodes.

An example of a further embodiment, which can be referred to as item 17, is the apparatus of item 11, wherein the channel and voltage for the negative DEP force experienced by the particle are designed to be stronger than the hydrodynamic drag; wherein conventional negative DEP levitation on top of the electrode and under the covert to trap particles in place with; and further comprising a detector for detecting the trapped particles.

An example of a further embodiment, which can be referred to as item 18, is the apparatus of item 11, further comprising side channels to separate particles, in response to the particles interacting with the electrodes, by size via.

An example of a further embodiment, which can be referred to as item 19, is the apparatus of item 11 further comprising at least one of an antenna, a transmitter, and associated circuitry to transmit wirelessly to a device; an antenna, a received to communicate wirelessly to a device; and circuitry to connect physically with a device.

In another example of an embodiment of the current invention, which can be referred to item 20, is a computer program product embodied on a non-transitory computer-readable medium in which a computer program is stored that, when being executed by a computer, would be configured to provide instructions to control or carry out applying a fluid sample into a microfluidic channel, wherein the microfluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured; generating highly localized modulated electric field distribution inside the channel and the fluid sample using the two-dimensional conducting materials; based on the generating, inducing DEP forces, wherein the DEP forces are the same or greater than DEP forces that would use metallic electrodes due to the sharp edges enabled by the two-dimension geometry of the two-dimensional conducting materials; and in response to the inducing, separating micro/nano-particles in the fluid sample into particles that respond to a negative DEP force and particles that respond to a positive DEP.

In another example of an embodiment of the current invention, which can be referred to as item 21, is an apparatus comprising means for accepting an application of a fluid sample into a microfluidic channel, wherein the micro fluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured; means for generating a highly localized modulated electric field distributions inside the channel and the fluid sample using the two-dimensional conducting materials; based on the generating, means for inducing DEP forces, wherein the DEP forces are the same or greater than DEP forces that would use metallic electrodes due to the sharp edges enabled by the two-dimension geometry of the two-dimensional conducting materials; in response to the inducing, means for separating micro/nano-particles in the fluid sample into particles that respond to a negative DEP force and particles that respond to a positive DEP.

An example of a further embodiment, which can be referred to as item 22, is the apparatus of item 21, further comprising means for determining the number of separated particles, where these separated particles are separated by means for separating micro/nano-particles in the fluid sample into particles that respond to a negative DEP force and particles that respond to a positive DEP and/or by means of side channels to separate particles by size, in response to the particles interacting with the electrodes.

An example of a further embodiment, which can be referred to as item 23, is the apparatus of item 22, further comprising means for ascertaining characteristics of the fluid sample based on the determining.

An example of a further embodiment, which can be referred to as item 24, is the apparatus of item 21 or 22, further comprising means for at least one of displaying, printing, indicating, or transmitting the ascertained characteristics or determined numbers.

An example of a further embodiment, which can be referred to as item 255, is the apparatus of item 21, further comprising means for receiving information for controlling Or programming the apparatus.

It is also noted herein that while the above describes example embodiments of the invention, these descriptions should not be viewed in a limiting sense. Rather, there are several variations and modifications which may be made without departing from the scope of the present invention as defined in the appended claims.

What is claimed is:

1. A method, comprising:
    applying a fluid sample into a microfluidic channel, wherein the micro fluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured;
    generating highly localized modulated electric field distribution inside the channel and the fluid sample using the two-dimensional conducting materials;
    based on the generating, inducing DEP forces, wherein the DEP forces are the same or greater than DEP forces that would use metallic electrodes due to the sharp edges enabled by the two-dimension geometry of the two-dimensional conducting materials;
    in response to the inducing, separating micro/nano-particles in the fluid sample into particles that respond to a negative DEP force and particles that respond to a positive DEP; and
    in response to the particles interacting with the electrodes, separating particles via side channels by size.

2. The method of claim 1, wherein the two-dimensional conducting materials comprise graphene sheets.

3. The method of claim 1, wherein a microfluidic chip comprises the microfluidic channel.

4. The method of claim 3, wherein microfluidic chips can be fabricated and patterned using standard semiconductor manufacturing technology.

5. The method of claim 3, wherein the microfluidic chip further comprises a generator for the generating.

6. The method of claim 1, wherein the two-dimensional conducting materials can be patterned into any arbitrary shape inside and outside the channel, wherein the two-dimensional conducting materials acting as two-dimensional electrodes create a same or improved electric field modulation locally than metallic electrodes.

7. The method of claim 1, further comprising:
    designing the channel and voltage for the negative DEP force experienced by the particle to be stronger than the hydrodynamic drag;
    trapping particles in place with conventional negative DEP levitation on top of the electrode and under the cover; and
    detecting the trapped particles.

8. The method of claim 1, further comprising:
    determining, in response to the separating, numbers of particles that respond to a negative DEP force and of particles that respond to a positive DEP, wherein the determining can be done by at least one of:
    a microfluidic chip comprising the microfluidic channel and a microprocessor, and
    a device connecting to a microfluidic chip comprising the microfluidic channel, wherein the connecting can be a physical connection or a wireless connection.

9. The method of claim 8, further comprising:
outputting results of the determining.

10. An apparatus, comprising:
    a micro fluidic channel where a fluid sample can be applied into, wherein the micro fluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured; and
    a generator to generate highly localized modulated electric field distribution inside the channel and the fluid sample using the two-dimensional conducting materials,
    wherein based on said generating, DEP forces are induced, wherein the DEP forces are the same or greater than DEP forces that would use metallic electrodes due to the sharp edges enabled by the two-dimension geometry of the two-dimensional conducting materials,
    wherein in response to said inducing, micro/nano-particles in the fluid sample are separated into particles that respond to a negative DEP force and particles that respond to a positive DEP, and and wherein in response to the particles interacting with the electrodes, separating particles via side channels by size.

11. The apparatus of claim 10, wherein the two-dimensional conducting materials comprise graphene sheets.

12. The apparatus of claim 11, wherein microfluidic chips can be fabricated and patterned using standard semiconductor manufacturing technology.

13. The apparatus of claim 10, wherein a microfluidic chip comprises the apparatus.

14. The apparatus of claim 10, further comprising: at least one processor; and at least one memory including computer program code, wherein the at least one processor, in response to execution of the computer program code, is configured to cause the apparatus to control or perform at least one of:

depositing the fluid sample into the microfluidic channel;
generating the highly localized field distribution; and
in response said separating of particles, calculating a number of particles separated.

15. The apparatus of claim 10, wherein the two-dimensional conducting materials can be patterned into any arbitrary shape inside and outside the channel, wherein the two-dimensional conducting materials acting as two-dimensional electrodes create a same or improved electric field modulation locally than metallic electrodes.

16. The apparatus of claim 10,
wherein the channel and voltage for the negative DEP force experienced by the particle are designed to be stronger than the hydrodynamic drag;
wherein conventional negative DEP levitation on top of the electrode and under the covert to trap particles in place with; and
further comprising a detector for detecting the trapped particles.

17. The apparatus of claim 10, further comprising at least one of:
an antenna, a transmitter, and associated circuitry to transmit wirelessly to a device;
an antenna, a received to communicate wirelessly to a device; and
circuitry to connect physically with a device.

18. A computer program product comprising a computer-readable medium bearing computer program code embodied therein for use with a computer, the computer program code comprising code for performing or controlling:

applying a fluid sample into a microfluidic channel, wherein the microfluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured;

generating highly localized modulated electric field distribution inside the channel and the fluid sample using the two-dimensional conducting materials;

based on the generating, inducing DEP forces, wherein the DEP forces are the same or greater than DEP forces that would use metallic electrodes due to the sharp edges enabled by the two-dimension geometry of the two-dimensional conducting materials;

in response to the inducing, separating micro/nano-particles in the fluid sample into particles that respond to a negative DEP force and particles that respond to a positive DEP; and in response to the particles interacting with the electrodes, separating particles via side channels by size.

19. An apparatus comprising:

means for accepting an application of a fluid sample into a microfluidic channel, wherein the microfluidic channel comprises a cover opposite the bottom, wherein integrated into the top of bottom of the microfluidic channel are electrodes, wherein the electrodes comprise patterned two-dimensional conducting materials, wherein electrical contact of the patterned two-dimensional conducting materials is ensured;

means for generating a highly localized modulated electric field distributions inside the channel and the fluid sample using the two-dimensional conducting materials;

based on the generating, means for inducing DEP forces, wherein the DEP forces are the same or greater than DEP forces that would use metallic electrodes due to the sharp edges enabled by the two-dimension geometry of the two-dimensional conducting materials;

in response to the inducing, means for separating micro/nano-particles in the fluid sample into particles that respond to a negative DEP force and particles that respond to a positive DEP; and in response to the particles interacting with the electrodes, separating particles via side channels by size.

* * * * *